US008071346B2

(12) United States Patent
Eid et al.

(10) Patent No.: US 8,071,346 B2
(45) Date of Patent: *Dec. 6, 2011

(54) SYSTEM FOR THE MITIGATION OF PHOTODAMAGE IN ANALYTICAL REACTIONS

(75) Inventors: John Eid, Palo Alto, CA (US); Devon Murphy, Mountain View, CA (US); Geoffrey Otto, Santa Clara, CA (US); Stephen Turner, Menlo Park, CA (US)

(73) Assignee: Pacific Bioscience of California, Inc., Menlo Park, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 11/981,626

(22) Filed: Oct. 31, 2007

(65) Prior Publication Data

US 2008/0176316 A1 Jul. 24, 2008

Related U.S. Application Data

(63) Continuation of application No. 11/293,040, filed on Dec. 2, 2005, now abandoned.

(51) Int. Cl.
*C12N 9/96* (2006.01)
(52) U.S. Cl. ........ 435/188; 435/193; 435/183; 359/368; 359/391; 359/392
(58) Field of Classification Search .................. 435/188, 435/183, 193
See application file for complete search history.

(56) References Cited

U.S. PATENT DOCUMENTS

| | | | |
|---|---|---|---|
| 4,689,307 A | 8/1987 | Schwartz | |
| 4,979,824 A | 12/1990 | Mathies et al. | |
| 5,547,839 A | 8/1996 | Dower et al. | |
| 5,674,716 A | 10/1997 | Tabor et al. | |
| 5,821,058 A | 10/1998 | Smith et al. | |
| 5,866,331 A | 2/1999 | Singer et al. | |
| 6,190,685 B1 | 2/2001 | Karita | |
| 6,210,896 B1 | 4/2001 | Chan | |
| 6,296,810 B1 | 10/2001 | Ulmer | |
| 6,544,797 B1 | 4/2003 | Buechler et al. | |
| 6,818,395 B1 | 11/2004 | Quake et al. | |
| 6,869,764 B2 | 3/2005 | Williams et al. | |
| 6,953,659 B2 | 10/2005 | Jacobson et al. | |
| 6,982,146 B1 | 1/2006 | Schneider et al. | |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 2002/0064524 A1 | 5/2002 | Cevc | |
| 2002/0100896 A1 | 8/2002 | Koizumi et al. | |
| 2002/0102595 A1* | 8/2002 | Davis ............................... | 435/6 |
| 2002/0156037 A1 | 10/2002 | Volkin et al. | |
| 2003/0044781 A1* | 3/2003 | Korlach et al. ................. | 435/6 |
| 2003/0087259 A1* | 5/2003 | Clancy et al. .................. | 435/6 |
| 2003/0124576 A1 | 7/2003 | Kumar et al. | |
| 2003/0174992 A1* | 9/2003 | Levene et al. .................. | 385/129 |
| 2003/0186276 A1 | 10/2003 | Odedra | |
| 2003/0190647 A1 | 10/2003 | Odera | |
| 2003/0194740 A1 | 10/2003 | Williams | |
| 2003/0215862 A1 | 11/2003 | Parce et al. | |
| 2004/0048301 A1 | 3/2004 | Sood et al. | |
| 2004/0170585 A1 | 9/2004 | Berens et al. | |
| 2004/0224319 A1 | 11/2004 | Sood et al. | |
| 2005/0026847 A1 | 2/2005 | Jacobs et al. | |
| 2005/0141843 A1 | 6/2005 | Warden et al. | |
| 2005/0148027 A1 | 7/2005 | Pirrung et al. | |
| 2005/0233399 A1 | 10/2005 | Aebersold et al. | |
| 2005/0271705 A1 | 12/2005 | Hughes et al. | |
| 2006/0019267 A1* | 1/2006 | Quake .............................. | 435/6 |
| 2006/0229407 A1 | 10/2006 | Vogel et al. | |
| 2008/0299565 A1 | 12/2008 | Schneider et al. | |
| 2009/0202993 A1 | 8/2009 | Lagunavicius et al. | |

FOREIGN PATENT DOCUMENTS

| | | |
|---|---|---|
| EP | 0428000 A1 | 5/1991 |
| EP | 1105529 B1 | 11/2005 |
| JP | 2123303 A | 5/1990 |
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |

OTHER PUBLICATIONS

Notification Concerning Transmittal of International Preliminary Report on Patentability dated Apr. 2, 2009; International Preliminary Report on Patentability; Written Opinion of the International Searching Authority (all for corresponding International Application No. PCT/US2006/046025).
M. J. Levene, et al., "Zero-Mode Waveguides for Single-Molecule Analysis at High Concentrations," *Science*, 299:682-686 (Jan. 31, 2003).
Dittrich et al. (2001) "Photobleaching and Stabilization of Fluorophores Used for Sing-Molecule Analysis with One- and Two-Photon Excitation." Applied Physics B: Lasers and Optics, 73:829-837.
Giloh et al, (1982) "Fluorescence Microscopy: Reduced Photobleaching of Rhodamine and Fluorescein Protein Conjugates by N-Propyl Gallate." Science, 217(4566):1252-1255.
Song et al., (1996) "Influence of the Triplet Excited State on the Photobleaching Kinetics of Fluorescein in Microscopy." Biolophysical Journal, 70(6):2959-2968.
Subramanyam, Rajagopal et al, (2005) "Protective Effect of Active Oxygen Scavengers on Protein Degradation and Photochemical Function in Photosystem I Submembrane Fractions During Light Stress." The Febs Journal, 272(4):892-902.

(Continued)

*Primary Examiner* — Susan Hanley
(74) *Attorney, Agent, or Firm* — Deana A. Arnold

(57) ABSTRACT

Compositions, devices, systems and methods for reducing and/or preventing photodamage of one or more reactants in illuminated analytical reactions by one or more of incorporating photodamage mitigating agents within the reaction mixture and/or interrogating different observation regions of the reaction mixture for a period that is less than a photodamage threshold period.

8 Claims, 12 Drawing Sheets

OTHER PUBLICATIONS

Extended European Search Report from related case EP 06838800.8, dated May 11, 2010.

Debey et al., Israel J. Chem. (1970) 8:115-123.

Kapanidis et al., J. Chem. Phys (2002) 117(25):10953-10964.

Piston et al., "Molecular expressions optical microscopy primer: specialized techniques" webpage (2004) http://www.microscopy.fsu.edu/primer/techniques/fluorescence/multiphoton/multiphoton-intro.html.

Van Dijk et al., J. Phys. Chem. B (2004) 108:6479-6484.

Derwent Abstract (English) for JP 02123303 downloaded Apr. 20, 2009.

* cited by examiner

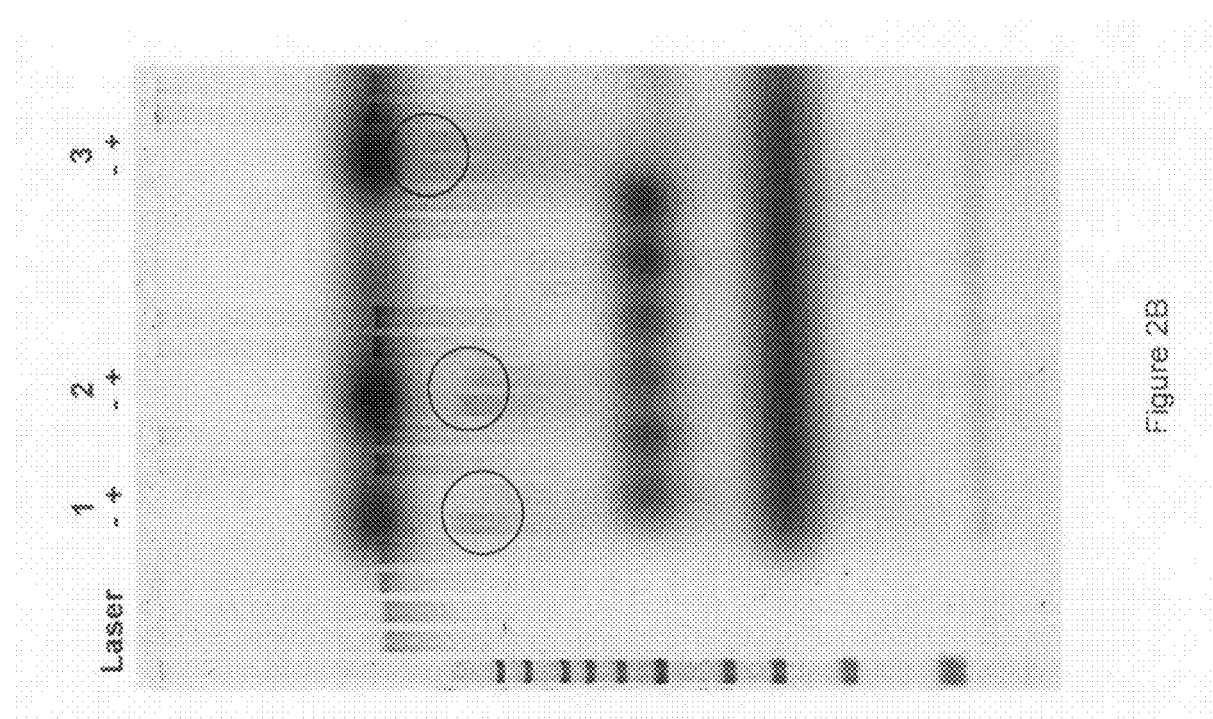

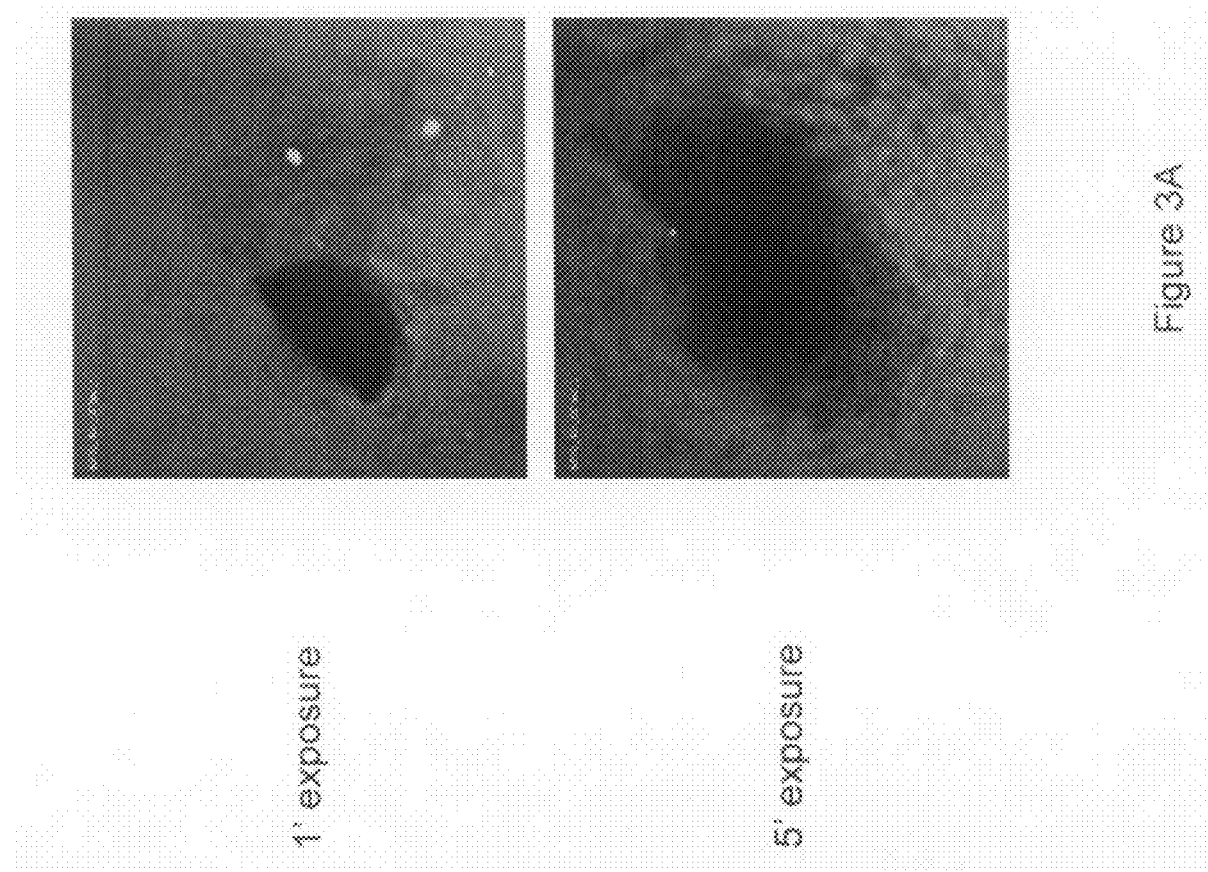

US 8,071,346 B2

SYSTEM FOR THE MITIGATION OF PHOTODAMAGE IN ANALYTICAL REACTIONS

CROSS-REFERENCE TO RELATED APPLICATIONS

This application is a continuation U.S. patent application Ser. No. 11/293,040 filed Dec. 2, 2005, now abandoned, the full disclosure of which is incorporated herein in its entirety for all purposes.

STATEMENT REGARDING FEDERALLY SPONSORED RESEARCH

A portion of this invention was made with government funding under NHGR1 Grant No. 1 R01 HG003710-01, and the government has certain rights in the invention.

BACKGROUND OF THE INVENTION

The use of optically detectable labeling groups, and particularly those groups having high quantum yields, e.g., fluorescent or chemiluminescent groups, is ubiquitous throughout the fields of analytical chemistry, biochemistry and biology. In particular, by providing a highly visible signal associated with a given reaction, one can better monitor that reaction as well as any potential effectors of that reaction. Such analyses are the basic tools of life science research in genomics, diagnostics, pharmaceutical research, and related fields.

To date, such analyses have generally been performed under conditions where the amounts of reactants are so far in excess that any adverse effects of the optical event would be unnoticed. For example, such analyses based upon fluorescent labeling groups generally require the use of an excitation radiation source directed at the reaction mixture, to excite the fluorescent labeling group, which is then separately detectable. However, prolonged exposure of chemical and biochemical reactants to such light sources, alone, or when in the presence of other components, e.g., the fluorescent groups, can lead, potentially, to damage to such reactants, e.g., proteins, enzymes, substrates, or the like. As noted previously, however, the existing formats for such reactions generally prevents any such effects from being problematic, or even being noticed.

A variety of analytical techniques are being explored, however, that deviate from the previous formats, such that detrimental effects of such photodamage will have a more dramatic impact on the operation of the given analysis. In particular, real time analyses of reactions that include fluorescent reagents can expose multiple different components to optical energy. Additionally, reactions based upon increasingly smaller amounts of reagents, e.g., in microfluidic or nanofluidic reaction vessels or channels, or in "single molecule" analyses. As such, the present invention is directed at methods and compositions that prevent or mitigate to some extent, the adverse effects of such photodamage, and also to processes that benefit from such methods and/or compositions, among other useful processes and compositions.

BRIEF SUMMARY OF THE INVENTION

The present invention is generally directed to compositions, devices, systems and methods for reducing and/or eliminating photodamage and its effects in illuminated reactions, and particularly those that utilize fluorescent and/or fluorogenic reactants.

In at least a first aspect, the invention provides a composition that comprises a first reactant, a second reactant, and a photodamage mitigating agent, where interaction of the first reactant with the second reactant under excitation illumination causes photodamage to the first reactant in the absence of the photodamage mitigating agent.

Relatedly, the invention further provides a composition that comprises a confined enzyme, a substrate for said enzyme, wherein interaction of the enzyme with the substrate under excitation illumination causes photodamage to the first reactant in the absence of a photodamage mitigating agent, and a photodamage mitigating agent.

The invention also provides devices that comprise a substrate having an observation region, a first reactant immobilized within the observation region, a second reactant disposed within the observation region, wherein interaction between the first and second reactants under excitation illumination causes photodamage to the first reactant, and a photodamage mitigating agent disposed within the observation region.

The invention also provides methods of performing an illuminated reaction, comprising providing a substrate having a reaction mixture disposed thereon, wherein the reaction mixture comprises a first reactant, a second reactant and a photodamage mitigating agent, wherein the photodamage mitigating agent reduces an amount of photodamage to the first reactant resulting from interaction of the first reactant with the second reactant under excitation illumination that would occur in the absence of the photodamage mitigating agent. The reaction mixture is then illuminated on the substrate, with an excitation illumination.

In additional aspects, the invention provides methods of performing an enzyme reaction, comprising providing an enzyme within a first observation region. The enzyme is contacted with a fluorescent or fluorogenic substrate for the enzyme, and an excitation radiation is directed at and signals are detected from the first observation region for a period that is less than a photodamage threshold period.

Similarly, in other aspects, the invention provides methods of monitoring a base extension reaction, comprising providing a polymerase enzyme within a first observation region, contacting the polymerase with at least a first fluorescent or fluorogenic nucleotide analog, and monitoring a fluorescent signal emitted from the first observation region in response to illumination with excitation radiation for a period that is less than a photodamage threshold period.

The invention also includes a system for analyzing an illuminated reaction that is susceptible to photodamage when illuminated for a period longer than an photodamage threshold period. The system typically comprises a substrate having reagents for the reaction disposed thereon, a mounting stage supporting the substrate and configured to receive the substrate, an optical train positioned to be in optical communication with at least a portion of the substrate to illuminate the portion of the substrate and detect signals emanating therefrom, and a translation system operably coupled to the mounting stage or the optical train for moving one of the optical train and the substrate relative to the other.

Also provided are methods of performing an enzyme reaction, comprising providing an enzyme within an observation region, and contacting the enzyme with a fluorescent or fluorogenic substrate for the enzyme under excitation illumination, in the presence of at least a first photodamage mitigating agent.

Other methods of the invention include methods of monitoring a base extension reaction, comprising providing a polymerase enzyme within an observation region, contacting the polymerase with at least a first fluorescent or fluorogenic nucleotide analog in the presence of at least a first photodamage mitigating agent, and monitoring a fluorescent signal emitted from the observation region in response to illumination with excitation radiation.

Also included are methods of monitoring a reaction mixture comprising at least a first enzyme and a fluorescent or fluorogenic substrate for the first enzyme, where the method comprises directing an excitation radiation at a first observation region for a first period that is less than a photodamage threshold period.

BRIEF DESCRIPTION OF THE DRAWINGS

FIG. 2A-2B are images of agarose gels of DNA synthesis products made in the presence of fluorescent nucleotide analogs and under selective illumination with laser excitation light. Shown are products of synthesis reaction mixtures in the presence and absence of different photodamage mitigating agents.

FIGS. 3A-3C are images of DNA synthesized on a planar substrate using fluorescent nucleotide analogs while being selectively illuminated at the excitation wavelengths of the fluorescent analogs. Shown are substrates subjected to the reaction mixtures in the presence and absence of different photodamage mitigating agents.

DETAILED DESCRIPTION OF THE INVENTION

The present invention is generally directed to methods of performing improved illuminated reactions, and particularly reactions that employ fluorescent or fluorogenic reactants, that mitigate the effects of and/or reduce photodamage to the various reactants present in such reactions. The invention includes methods for preventing or reducing such photodamage as well as methods for mitigating the impacts such photodamage might have on an overall analysis, as well as combinations of these.

While the invention is generally applicable to any of a variety of optical assays that require substantial illumination and/or photoactivated conversion or excitation of chemical groups, e.g., fluorophores, it finds greatest utility in analyses that utilize very limited concentrations of reactants that might be subject to photodamage. As will be appreciated, in such reagent limited analyses, any degradation of a critical reagent will dramatically impact the analysis, by further limiting the reagent.

One particularly apt example of analyses that benefit from the invention are single molecule biological analyses, including, inter alia, single molecule nucleic acid sequencing analyses, single molecule enzyme analyses, hybridization assays, e.g., antibody assays, nucleic acid hybridization assays, and the like, where the reagents of primary import are subjected to prolonged illumination with relatively concentrated light sources, e.g., lasers or other concentrated light sources, i.e., mercury, xenon, halogen or other lamps, in an environment where photoconversion/excitation is occurring, with its associated generation of products.

Figure 1:
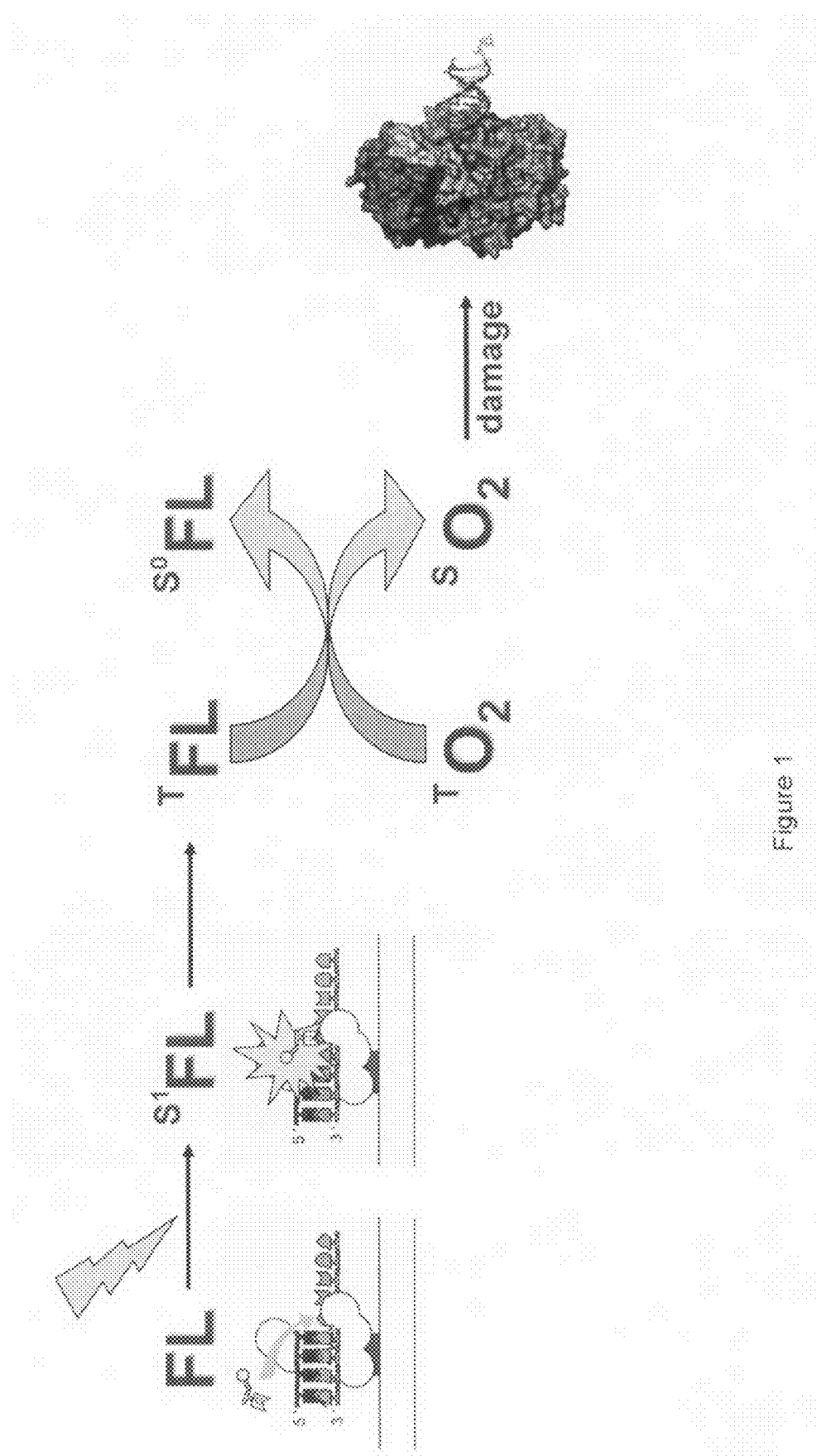
FIG. 1 is a schematic illustration of a proposed mechanism of photodamage to DNA polymerase in template dependent synthesis using fluorescent nucleotide analogs while under excitation illumination.

With reference to nucleic acid analyses, it has been observed that in template directed synthesis of nucleic acids using fluorescent nucleotide analogs as the substrate, that prolonged illumination under such conditions yields substantial degradation in the ability of the polymerase to synthesize such DNA (See FIG. 3A, and Example 1). Damage or even inactivation of polymerase enzymes can seriously detract from the ability of the polymerase to process longer strands of nucleic acids. This reduction in processivity of the enzyme, in turn, leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA. A proposed mechanism for this photodamage is shown in FIG. 1. As shown, a fluorophore excited by exposure to electromagnetic radiation at an excitation wavelength can transition into a triplet state. Subsequent relaxation of the triplet state fluorophore can then lead to generation of reactive oxygen species, which can, in turn, damage one or both of the fluorophore or the enzyme processing the fluorophore, e.g., the polymerase. Accordingly, oxygen scavengers and/or reducing agents are included to prevent the formation of reactive oxygen.

In general terms, the invention is generally directed to the performance of illuminated reaction analyses, where such analyses are illuminated for an amount of time that still permits the effective performance of the analysis. In particularly preferred aspects, illuminated analysis refers to an analytical reaction that is occurring while being illuminated, e.g., with excitation radiation, so as to evaluate the production, consumption and/or conversion of luminescent, e.g., fluorescent reactants and/or products As used herein, the amount of time an illuminated analysis may be carried out before photodamage so substantially impacts the reactants to render the analysis non-useful, is referred to as the photodamage threshold period. In terms of the invention, the photodamage threshold period is preferably that period of illuminated analysis during which such photodamage occurs so as to reduce the rate of the subject reaction by at least 20% over the same reaction in the absence of such illumination, more preferably, more than 50%, and in some cases, more than 90%, e.g., causing a 90% reduction in the reaction rate of the system, or a 90% reduction in the amount of product produced during a given time frame. It is an object of the invention to perform an illuminated analysis within the photodamage threshold period. This is generally accomplished in alternative ways. First, performing a given reaction within the foregoing parameters and in accordance with the invention or aspects thereof, may include performing the reaction for a period of time that is less than the photodamage threshold period. Second, the reaction may be configured to increase the length of the photodamage threshold period, or third, it may include a combination of these approaches.

As will be appreciated, the photodamage sought to be prevented by the methods and compositions of the invention is not merely photodamage to fluorescent reagents, e.g., photobleaching, but is instead directed to prevention or reduction of the downstream effects of such photodamage to other reagents that are of limited quantity in a reaction mixture, and as such, their limited presence is more greatly impacted by even slight losses due to photodamage, and particularly reactive proteins or enzymes, which, without being bound to a theory of operation, may include damage to the enzymes or reactive proteins or irreversible interactions between such enzymes or proteins and the photodamaged reagents. As suggested by the foregoing, photodamage generally refers to an alteration in a given reagent, reactant or the like, that causes such reagent to have altered functionality in a desired reaction, e.g., reduced activity, reduced specificity, or a reduced ability to be acted upon, converted, or modified, by another molecule, that results from, either directly or indirectly, a photo-induced reaction, e.g., a photo-induced reaction creates a damaged reactant that interacts with and causes damage to one or more other reactants. Typically, such photoreaction directly impacts either the reactant of interest, e.g., direct photodamage, or impacts a reactant within one, two or three reactive steps of such reactant of interest.

As generally referred to herein, such limited quantity reagents or reactants may be present in solution, but at very limited concentrations, e.g., less than 200 nM, in some cases less than 10 nM and in still other cases, less than 10 pM. In preferred aspects, however, such limited quantity reagents or reactants refer to reactants that are immobilized, or otherwise confined within a given area, so as to provide limited quantity of reagents in that given area, and in certain cases, provide small numbers of molecules of such reagents within that given area, e.g., from 1 to 1000 individual molecules, preferably between 1 and 10 molecules. As will be appreciated, photodamage of immobilized reactants in a given area will have a substantial impact on the reactivity of that area, as other, non-damaged reactants are not free to diffuse into, and mask the damage effects.

While researchers have provided methods and compositions for limiting photodamage to fluorophores, the negative impacts of downstream photodamage to enzymatic systems in the presence of and/or resulting from photodestruction of fluorescent reagents has not been readily recognized or addressed. For ease of discussion, the detrimental impact of the photodamage event, whether resulting from actual damage to a given reagent or from interaction with a damaged reagent, is generally referred to herein as photodamage.

I. PREVENTION OF PHOTODAMAGE

In a first aspect, the invention is directed to methods and compositions that reduce the amount of photodamage that is done to one or more non-fluorescent reactants during illumination, e.g., with an excitation radiation source. In particular, compositions are provided that yield a reduction in the level of photodamage (or an increase in the photodamage threshold period) as compared to such reactions in the absence of such compositions. As used herein, the components of such compositions that provide such effects are generally referred to as photodamage mitigating agents. In particular, photodamage mitigating agents are provided in the context of the analytical reaction to reduce the level of photodamage (and/or increase the photodamage threshold period), that would otherwise have occurred but for the presence of the photodamage mitigating agent.

Again, the definition of an agent as a photodamage mitigating agent is generally reflective of the impact that such agent has on the actual photodamage event or the downstream impacts of that damage. As such, a photodamage mitigating agent may prevent photodamage of one or more reagents, or it may mitigate the impact that a photodamaged reagent may have on a particular, limited reagent in the reaction of interest. By way of example, an agent that blocks a detrimental interaction between a photodamaged fluorescent compound and a critical enzyme component would still be referred to as a photodamage mitigating agent, regardless of the fact that it did not prevent the initial photodamage to the fluorescent reagent.

Measurements of reduction of photodamage as a result of inclusion or treatment with a photodamage mitigating agent may be characterized as providing a reduction in the level of photodamage over an untreated reaction. Further, characterization of a reduction in photodamage generally utilizes a comparison of reaction rates, e.g., enzyme activity, and/or a comparison of the photodamage threshold period, between a treated reaction mixture and an untreated reaction mixture.

In the case of the present invention, the inclusion of photodamage mitigating agent(s) of the invention generally results in a reduction of photodamage of one or more reactants in a given reaction, as measured in terms of prevented loss of reactivity, e.g., enzyme activity, in the system, of at least 10%, preferably, greater than 20%, and more preferably, greater than about a 50% reduction, and in many cases greater than a 90% and up to and greater than 99% reduction in such photodamage. By way of illustration, and purely for the purpose of example, when referring to reduction in photodamage as a measure of enzyme activity in the presence and absence of the photodamage mitigating agent, if a reaction included a reaction mixture having 100 units of enzyme activity that would, in the absence of a photodamage mitigating agent, and following illuminated analysis, yield a reaction mixture having only 50 units of activity, then a 10% reduction in photodamage would yield a final reaction mixture of 55 units (e.g., 10% of the 50 units otherwise lost, would no longer be lost).

Without being bound to a particular theory or mechanism of operation, it is believed that at least one cause of photo-induced damage to enzyme activity, particularly in the presence of fluorescence reagents, results from the direct interaction of the enzyme with photodamaged fluorescent reagents. Further, it is believed that this photodamage of the fluorescent reagents (and possibly additional damage to the enzyme) is at least partially mediated by reactive oxygen species that are generated during the relaxation of triplet state fluorophores in the presence of molecular oxygen.

Accordingly, in at least a first aspect, the present invention is directed to the inclusion within the illuminated reaction mixture of one or more agents that function to block or otherwise minimize the pathways that lead to such photodamage. Such agents include reducing agents or anti-fade agents that prevent the formation of the triplet state fluorophores (also referred to as triplet state quenchers), as well as oxygen scavenging agents, that remove oxygen and reactive oxygen species from the reaction mixture, thus preventing downstream damage to enzymes within the system.

A variety of reducing agents or anti-fade agents may be used as triplet state quenchers, including, for example, ascorbic acid, dithiothreitol (DTT), mercaptoethylamine (MEA), β-mercaptoethanol (BME), n-propyl gallate, p-phenylenediamene (PPD), hydroquinone, sodium azide ($NaN_3$), diazobicyclooctane (DABCO), as well as commercially available anti fade agents, such as Fluoroguard (available from BioRad Laboratories, Inc., Hercules, Calif.), Citifluor antifadants (Citifluor, Ltd., London, UK), ProLong, SlowFade, and SlowFade Light (Invitrogen/Molecular Probes, Eugene, Oreg.).

Likewise, a number of singlet oxygen quenchers may be used to eliminate or reduce reactive oxygen species, including, for example, enzymatic systems, e.g., superoxide dimutase, glucose oxidase/catalase (GO/Cat), glutathione peroxidase, or combinations of these with other enzymes, or thiol based quenchers e.g. ergothioneine, methionine, cysteine, beta-dimethyl cysteine (penicillamine), mercaptopropionylglycine, MESNA, glutathione, dithiothreitol (as noted above for a reducing agent), N-acetyl cysteine and captopril (See, e.g., Biochem Soc. Trans. 1990 December; 18(6): 1054-6). Also, biological singlet oxygen quenchers may be employed such as lycopene, gamma-carotene, astazanthin, canthazanthin, alpha-carotene, beta-carotene, and its analogs (See, e.g., Carcinogenesis vol. 18 no. 1 pp. 89-92, 1997), bixin, zeaxanthin, lutein, bilirubin, biliverdin, and tocopherols (See, e.g., Biochem Soc Trans. 1990 December; 18(6): 1054-6 ref.) as well as polyene dialdehydes (Carcinogenesis vol. 18 no. 1 pp. 89-92, 1997) melatonin, vitamins E ($\alpha$-tocopheryl succinate and its analogs) and $B_6$ (pyridoxine1 and its derivatives). Other chemical oxygen scavengers are also available, e.g., hydrazine ($N_2H_4$), sodium sulfite ($Na_2SO_3$), hydroxylamine, glutathione, and N-acetylcysteine, and the like. In addition to the foregoing, in many cases, the amount of singlet oxygen quenchers or scavengers may be reduced or eliminated by physically excluding oxygen from the reaction of interest by, e.g., degassing reagents, perfusion with inert gases, or the like.

In accordance with the present invention, photodamage mitigating agents may generally be provided as a component of the reaction mixture, either through addition as an additive, either liquid or solid, or through predisposition and/or immobilization of the photodamage mitigating agents within the region where the reaction is taking place. By way of example, in cases where the reaction of interest is confined to a particular region or location, it may be desirable to immobilize or otherwise localize the photodamage mitigating agents within or proximal to that region. Likewise, where photodamage mitigating agent comprises cooperatively functioning components, e.g., dual enzyme systems, it may again be desirable to localize such components relative to each other, as well as to the reaction of interest.

II. MITIGATION OF PHOTODAMAGE IMPACTS

In contrast and/or in addition to the use of photodamage mitigating agents, the present invention also provides methods of mitigating the impact of photodamage on the results of a given analytical operation by only interrogating a reaction mixture, e.g., detecting fluorescent emission, during such portion of the illumination period before which excessive photodamage has occurred. This approach is particularly useful in the optical interrogation of reactions where components of the reaction that are susceptible to photodamage are spatially confined on an assay plate or substrate, either through the presence of structural confinements and/or through immobilization of the components. Examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflectance microscopy or fluorometry, surface imaging, or the like.

As used herein, a substrate may comprise any of a variety of formats, from planar substrates, e.g., glass slides or planar surfaces within a larger structure, e.g., a multi-well plates such as 96 well, 384 well and 1536 well plates or regularly spaced micro- or nano-porous substrates, or such substrates may comprise more irregular porous materials, such as membranes, aerogels, fibrous mats, or the like, or they may comprise particulate substrates, e.g., beads, spheres, metal or semiconductor nanoparticles, or the like. In addition, for purposes of discussion herein, whether a particular reagent is confined by virtue of structural barriers to its free movement, or is chemically tethered or immobilized to a surface of a substrate, it will be described as being "confined".

For example, in interrogating an enzyme reaction where such photodamage can occur and where the enzyme is immobilized upon a substrate surface, prolonged exposure of a particular region will result in photodamage to or "burning in" of the enzyme immobilized within that region. In a number of cases, a selected region of a substrate, including the reaction of interest will be interrogated. For purposes of discussion, such region is termed an "observation region."

In accordance with the present invention, the "burn in" or at least the effects of such burn in, are reduced or eliminated by illuminating and collecting emission signals from a different observation region. For ease of discussion, the action of both illuminating and collecting emission signals from a reaction of interest, or a particular observation region in which a reaction of interest is taking place, is referred to as interrogating that reaction and/or that region. As will be appreciated, interrogating a new observation region of a substrate will constitute newly illuminating a region and collecting emission signals from that newly illuminated region. Rephrased, as long as one is interrogating a newly illuminated region, whether the burned region is still being illuminated is not of major import, unless one is desirous of returning to interrogate that region at a later time.

Figure 5:
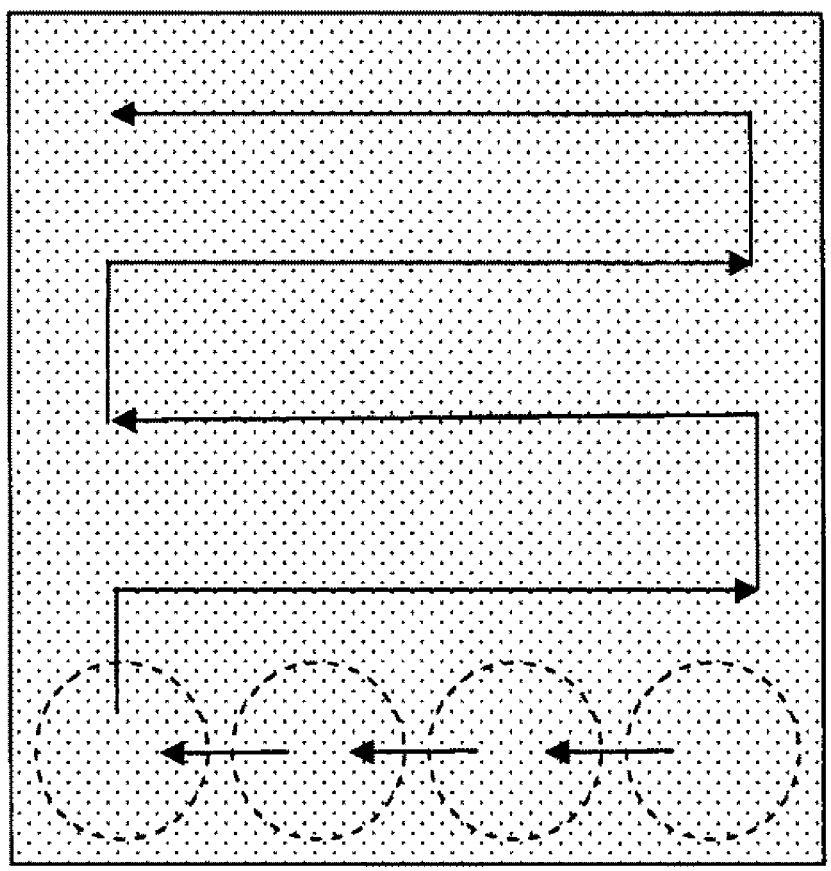
FIG. 5 is a schematic illustration of a step and repeat analysis method to avoid the impacts of excessive photodamage on assay substrates.

In addition to the advantages of reducing photodamage, the process of interrogating different regions of a substrate over time also provides benefits of being able to interrogate larger substrate areas with a given light source than would have otherwise been possible without modifying the nature of the illumination, e.g., expanding a laser spot size by changing the illumination angle, e.g., to provide an elongated laser spot size (See, e.g., U.S. Pat. No. 6,881,312, incorporated herein by reference in its entirety for all purposes), or passing the illumination through an optical train that alters the shape of the incident light spot on the substrate, e.g., providing a cylindrical lens to provide the illumination in a line format, or otherwise refocusing the illumination to provide an expanded spot size or dimension. Notwithstanding the foregoing, it will be appreciated that the present invention is optionally combined with such optics that provide an expanded illumination area, that is optionally used in addition to processes where such expanded illumination profile is then moved over the substrate to interrogate different regions of the substrate over time. FIG. 5 illustrates the movement of an interrogation spot region over a substrate upon which a reaction of interest is being carried out, over time, to interrogate different regions of a substrate. As will be appreciated, used of a linear illumination spot over the substrate would more rapidly illuminate larger areas of the substrate than the circular spot shown in FIG. 5. As shown in FIG. 5, the exemplary substrate comprises a plurality of arrays of smaller structural confinements (that also function as optical confinements in the form of zero mode waveguides), where each array or subset of arrays are included within a separate structural confinement, e.g., a well in a multiwell substrate or plate. As will be appreciated, the interrogation function typically is carried out over a given region for a prolonged period of time that is not longer than the photodamage threshold period. Typically, this will be for greater than 10 seconds, preferably greater than 1 minute, more preferably greater than 5 minutes, greater than 10 minutes, greater than 20 minutes, and in some cases, greater than 2 hours or greater than 3 or more hours, but still less than the photodamage threshold period.

In addition to gaining additional interrogation area by moving the interrogation region over the area of the substrate, the ability to move that region, also provides an ability to adjust the mechanical interfaces with the substrate in a particular system or apparatus, so as to make regions available for interrogation that may have been otherwise un-interrogatable in the particular system or apparatus. In particular, in a typical substrate analysis set-up, a substrate to be analyzed is fixed upon an analysis stage where portions of that substrate may be obscured from interrogation by the mounting structure of the analysis stage, e.g., clips, support structures, or the like. In accordance with certain aspects of the invention, however, the movement of the interrogation region provides the ability to alter, over time, the portions of the substrate that are obscured by the mounting structures. In a first example, rather than moving the optical train that provides illumination to a given region of the substrate, the substrate may be moved relative to the interrogation optics. This may be accomplished using any of a variety of manipulation hardware or robotic set-ups. For example, a stepper/feeder apparatus is used that steps the substrate through the interrogation zone of the optical train in a precise fashion. Such precise feeder apparatus' are well known in high performance printing technologies, as well as in translational robotics used in the semiconductor industry, e.g., in both analytical and manufacturing applications. Such stepper feeders may include a roller or wheel assembly that contacts an upper surface of the overall substrate, and is rotated to provide motive force to the substrate in a precise fashion, to feed that substrate through the interrogation zone of the optical train. In alternative aspects robotic systems may be used to pick-up and re-orient a given substrate in order to interrogate different regions of the substrate surface, or make a previously inaccessible region of the substrate accessible. Such robotic systems are generally available from, e.g., Beckman, Inc., Tecan, Inc., Caliper Life Sciences, and the like.

In accordance with the invention, a reaction of interest within a first observation region is interrogated for a time period that is less than a photodamage threshold period, as set forth elsewhere herein, and then the reaction of interest in a second, different observation region is interrogated. In accordance with the present invention, the observation typically includes confined reagents that are susceptible to photodamage. As such, an observation region may include an area of a planar or other substrate surface upon which are immobilized reagents, e.g., enzymes. Alternatively, the observation region may include a physical confinement that constrains the reagents that are susceptible to photodamage, including, e.g., microwells, nanowells, planar surfaces that include hydrophobic barriers to confine reagents. As noted above, the present invention is particularly applicable to observation regions in which the damage susceptible reagents are present at concentrations or levels that photodamage greatly impacts the reaction progress. This is particularly the case in immobilized reaction systems where additional, excess amounts of reagents can not be provided in a bulk solution to obscure the impact of any damaged reagents.

The sequential interrogation of different observation regions may generally be repeated a large number of times, e.g., more than 10, more than 100 more than 1000, or even more than 10,000 times, so long as observation regions remain. The availability of multiple regions is generally limited only by the size of a discrete observation region, which may be defined by one or more of the nature and dimensions of any structural confinements used, and the illumination spot size, and the overall area of the analytical substrate. In general, this method of stepping the interrogation region to another, preferably adjacent region, and repeating the interrogation process is generally referred to as a "step and repeat" process.

Figure 6B:
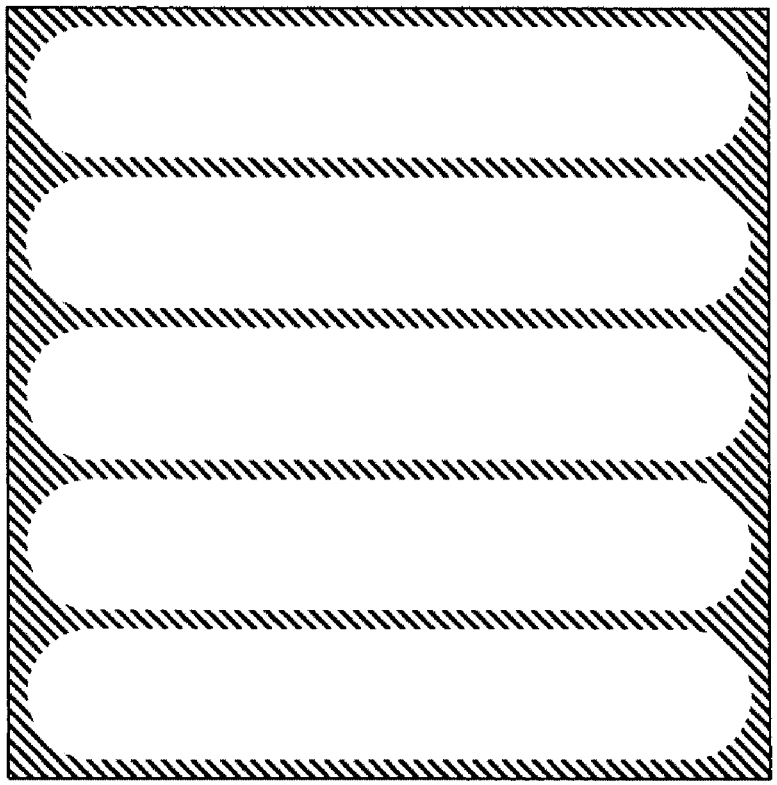
FIGS. 6A and 6B provide a schematic comparison of a non-overlapping step and repeat interrogation and a scan mode interrogation.
Figure 6A:
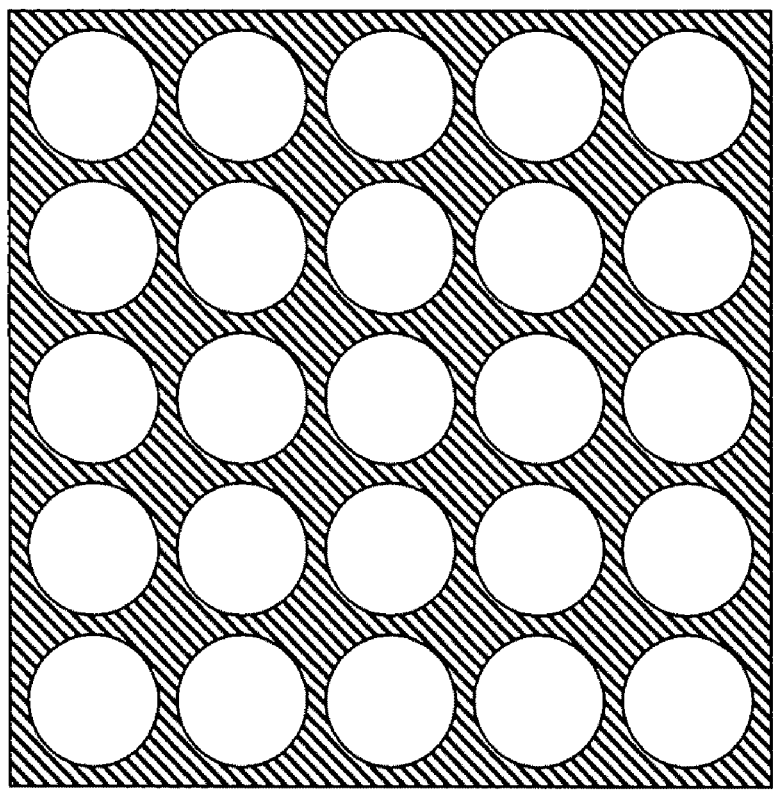

Although described as a "step and repeat" method, in some embodiments where the interrogation region is moved across a substrate, that movement is not step-wise and iterative, but instead constitutes a continuous motion, substantially continuous motion or a stepped movement or iterative motion whereby each iterative step interrogates a new region that overlaps with some portion of the previously interrogated region or of the interrogation region across the substrate. In particular, a substrate may be moved continuously through an interrogation zone of an optical system, whereby the interrogation region moves continuously across the substrate being interrogated (in a "scan mode"). In accordance with preferred aspects, the speed of movement of the interrogation region is dictated by the amount of time a given reaction zone, e.g., a structural or optical confinement, ZMW, or the like, is desired to stay within the interrogation region, e.g., for a period less than the photodamage threshold period. FIG. 6A shows a schematic illustration of a non-overlapping step and repeat interrogation method using a circular illumination spot. As shown, some portion of the substrate surface, indicated by hatching, is not subjected to interrogation. In FIG. 6B, however, a scanning or overlapping stepping process is used to interrogate larger portions of the surface area.

Figure 7:
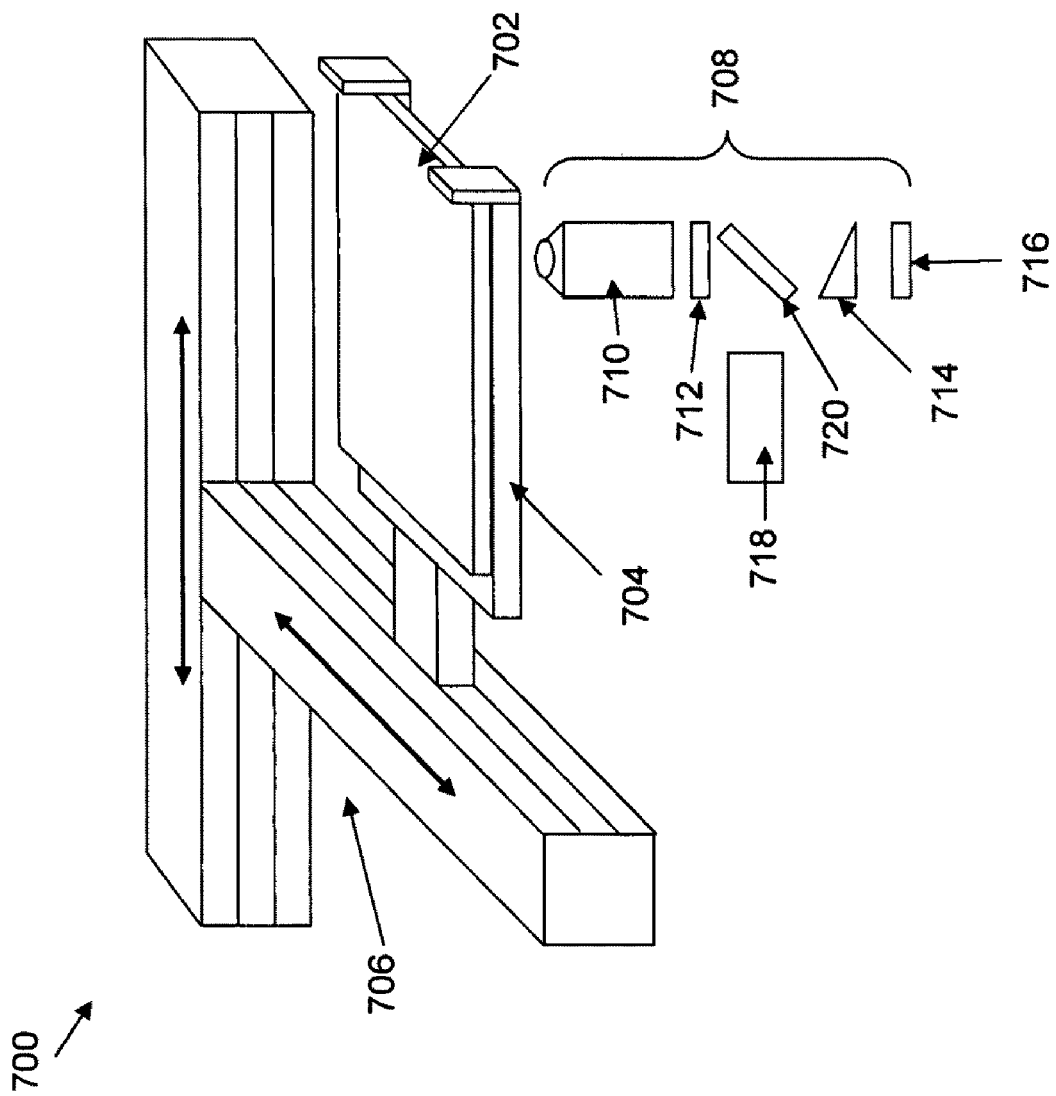
FIG. 7 is a schematic illustration of a system for carrying out certain aspects of the invention.

FIG. 7 is a schematic illustration of an overall system 700 useful for performing the step and move operations on substrates in accordance with certain aspects of the invention. As shown, a reaction substrate 702 is disposed upon a translation stage 704. Stage 704 is typically coupled to appropriate robotics (schematically represented by armature 706) that provides lateral translation of the substrate 702, in two dimensions (x and y) over a fixed optical train 708. Although shown as being coupled to and rendering the translation of the substrate, it will be appreciated that alternative configurations could couple to translation system to the optical train to move that aspect of the system relative to the substrate. Optical train 708 may comprise a variety of different configurations useful for interrogating the substrate, including appropriate excitation light sources, e.g., laser 718, focusing and filtering optics, e.g., dichroic mirror 720, objective lens 710, imaging lens 712, prism 714, and detectors or detector arrays, e.g., detector array 716. One example of a particularly preferred optical train is described in commonly owned U.S. patent application Ser. No. 11/201,768 filed Aug. 11, 2005, and incorporated herein by reference in its entirety for all purposes.

III. EXEMPLARY APPLICATIONS

As noted above, the methods and compositions of the invention are useful in a broad range of optically detected analytical reactions, and particularly those using photoluminescent or fluorescent reactants, and particularly such reactions where the reagents that are susceptible to photodamage are present at relatively low levels. One exemplary application of the methods and compositions described herein is in single molecule analytical reactions, where the reaction of a single, or very limited number of molecules are observed in the analysis, such as observation of the action of a single enzyme molecule. In particular, when an analysis is relying upon a small population of reagent molecules, damage to any significant fraction of that population will have a substantial impact on the analysis being performed.

One example of a single molecule analysis includes sequencing of nucleic acids by observing incorporation of nucleotides into a nascent nucleic acid sequence during template directed polymerase based synthesis. Such methods, generally referred to as "sequencing by incorporation," involve the observation of the addition of nucleotides or nucleotide analogs in a template dependent fashion in order to determine the sequence of the template strand. A number of processes for performing this detection include the use of fluorescently labeled nucleotide analogs within a confined observation region, e.g., within a nanoscale well or tethered, either directly or indirectly to a surface. By illuminating and detecting the fluorescent bases that are incorporated, or are to be incorporated into the nascent strand, one can ascertain the nature of the base, and as a result, the complementary base in the template strand.

One particularly preferred aspect of the invention is in conjunction with the sequencing by incorporation of nucleic acids within an optical confinement, such as a zero mode waveguide, in which one is observing an extremely small reaction volume in which one or only a few polymerase enzymes and their fluorescent substrates may be present. Zero mode waveguides, and their use in sequencing applications is generally described in U.S. Pat. No. 6,917,726, and preferred methods of sequencing by incorporation are generally described in Published U.S. Patent Application No. 2003-0044781, the full disclosures of which are incorporated herein by reference in their entirety for all purposes.

As will be appreciated, prolonged interrogation of a limited population of reagents, e.g., fluorescent analogs and confined polymerase enzymes can lead to photodamage of the various reagents to the point of substantially impacting the activity or functionality of the polymerase enzyme. In particular, it has been shown that prolonged illumination of DNA polymerases involved in synthesis using fluorescent nucleotide analogs results in a dramatic decrease in the enzyme's ability to synthesize DNA. Without being bound to any theory of operation, it is believed that the photodamage event affects the catalytic region of the enzyme thus affecting either the ability of the enzyme to remain complexed with the template, or its ability to process additional synthesis.

In accordance with the present invention, the above-described sequencing reaction may be carried out in the presence of one or more photodamage mitigating agents, as described above. In preferred aspects, the sequencing reactions may be carried out in the presence of both a reducing agent, such as DTT, MEA or BME, and an oxygen scavenger, such as GO-Cat.

In general, the photodamage mitigating agents are present in the reaction mixture at levels sufficient to provide beneficial impact, e.g., reduced photodamage and/or extension of the photodamage threshold period, but are not present at such levels as to interfere with the reaction of interest, e.g., the sequencing reaction. Concentrations of the components of a photodamage mitigating agent will generally vary by application. By way of example, reducing agents, such as DTT, MEA or BME, may generally be present at amounts of between about 100 µM and 500 mM, and preferably between about 1 mM and about 200 mM, e.g., in some cases about 5 mM for DTT and 100 mM for MEA, but may vary from these concentrations. In the case of DTT, preferred concentrations range from about 1 mM to about 10 mM, while preferred ranges for MEA may be from about 10 mM to about 200 mM. Likewise, the concentration of oxygen scavengers will generally vary depending upon the application, the level of oxygen present, the susceptibility of the system to reactive oxygen species, etc. For example, in sequencing reactions, oxygen scavenging enzyme systems, e.g., GO-Cat, are generally present at levels that provide effective oxygen scavenging without excessively impairing the desired reactions, e.g., polymerase activity. Typically, this includes concentrations of GO-Cat reagents within the reaction mixture that are anywhere from, e.g., up to about 5 µM Glucose Oxidase and up to about 575 nM catalase, or 3 to 4 times typical GO-Cat concentrations, down to 13 nM Glucose Oxidase and 1.5 nM catalase) or 0.01×GO-Cat concentrations. Typically, the concentrations will be between about 0.01× to about 0.5× of typical GO-Cat concentrations as set forth above, and more preferably including or between about 0.1× and 0.25×GO-Cat. For immobilized oxygen mitigation systems, the amount of immobilized reagents will generally provide activity levels that correspond to the activity levels of the aforementioned concentrations in non-immobilized formats. Precise amounts of reagents will generally depend upon the relative efficiency of the immobilization process, and resulting activity of the immobilized components.

The following non-limiting examples are provided to further illuminate the invention.

IV. EXAMPLES

Because of the value of single molecule analysis in nucleic acid sequencing applications, DNA polymerase systems were used to identify the impact of photodamage and its solutions in accordance with the present invention. Initial assays were run in three different configurations to identify the scope and/or nature of photodamage to polymerase reactions. These included a bulk DNA synthesis experiment, a flat surface based nucleic acid synthesis reaction, and synthesis within an array of zero mode waveguides.

Example 1

Photodamage and Mitigation in Bulk Reaction Volumes

In a first assay, synthesis reaction mixtures contained a modified ($\phi$29 DNA polymerase, 300 nM DNA template, three native nucleoside triphosphates (at 10 µM each) and a fluorescent dye labeled nucleoside polyphosphate (at 10 µM) in synthesis buffer (50 mM Tris-HCl, pH 7.5, 75 mM KCL, 20 mM $(NH_4)_2SO_4$, 10 mM BME, 0.7 mM $MnCl_2$). Each of the reactions were carried out at room temperature (22° C.) for the desired illumination period, ranging from 1 minute to one hour.

The experiment included two sets each of three different reaction mixtures: (1) a synthesis reaction using only native, e.g., unlabeled nucleoside triphosphates; (2) a synthesis reaction including two native nucleoside triphosphates, an Alexa 488 labeled dCTP analog, and an Alexa 568 labeled dTTP; and (3) a synthesis reaction including two native nucleoside triphosphates, an Alexa 488 labeled dC4P analog (tetraphosphate), and an Alexa 568 labeled dT4P. Each different synthesis reaction conditions included either no illumination or laser illumination during synthesis for five minutes with wavelengths of 488, 568 and 647 nm, followed by 60 minutes of nonilluminated synthesis.

Figure 2A:
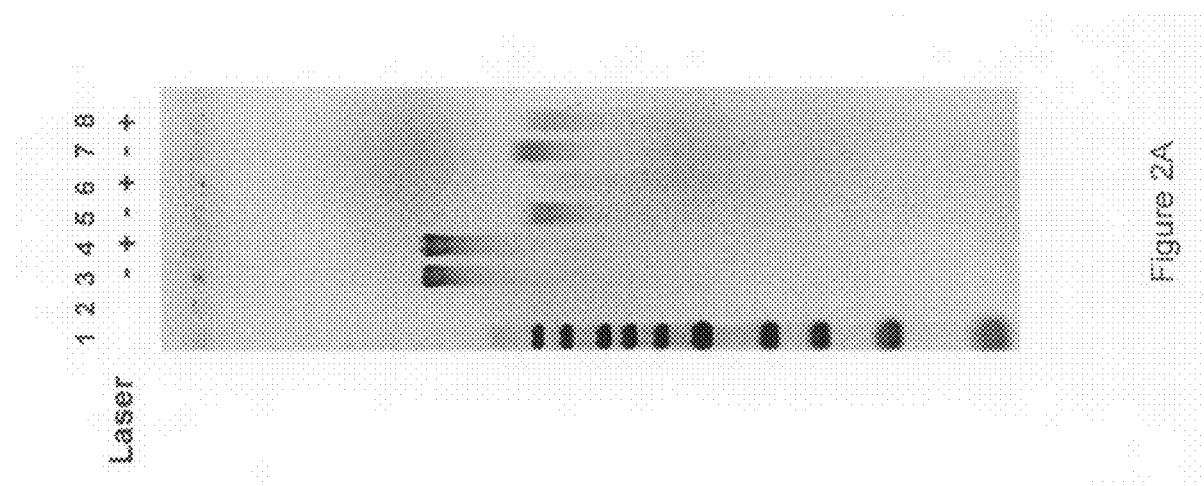

Following synthesis, the reaction products were separated on a 0.7% agarose gel under standard conditions. FIG. 2A provides an image of the Sybr® Gold stained gel. As shown, lane 1 on the left, includes a molecular weight standard. The next two lanes (3 and 4, lane 2 is empty)) include the synthesis reaction including only unlabelled nucleoside triphosphates (reaction conditions 1, above), in the absence of laser illumination (−) and with laser illumination (+). Moving to the next two lanes to the right (5 and 6) include similar reactions, but including labeled nucleoside triphosphates (reaction condition 2, above), while the right most lanes (7 and 8) include the labeled nucleoside tetraphosphate analogs in the synthesis reaction (reaction condition 3, above) (For a discussion of phosphate labeled nucleoside polyphosphates, see, e.g., U.S. Pat. No. 6,399,335, and published U.S. Patent Application No. 2003/0124576, the full disclosures of which are incorporated herein by reference for all purposes).

As can be seen from the gel, a large amount of relatively high molecular weight DNA has been synthesized in the native reaction, both with and without laser illumination. In each of the cases utilizing labeled analogs, the amount and relative size of the synthesized DNA is less than native conditions. Of particular note, however, is that in each of these latter two reactions, the laser illumination results in a substantial decrease in the amount of higher molecular weight DNA produced. Of further note, despite that reaction conditions are identical for reaction conditions 2 and 3, except for the use of tetraphosphate analogs, the amount of lost DNA synthesis in the illuminated sample is proportionately greater in the labeled triphosphate reaction. This is indicated by the ratio of DNA in the Illuminated sample to the nonilluminated sample for each reaction condition (as determined by image scanning). In particular, the ratio DNA quantity in the gel lane of illuminated to nonilluminated in the native reaction conditions is approximately 1 (1.10). When the reaction includes labeled triphosphate analogs, this ratio drops to 0.27, while the use of tetraphosphate analogs drops this ratio to 0.56. These data are suggestive that the photodamage effects may be caused by proximity or length of retention time of the fluorophor to the active site of the enzyme during illumination. This interpretation was strengthened by similar experiments performed with unlabeled nucleoside triphosphates, that were spiked with free dyes, e.g., not coupled to the analog, that showed little or no impact of illumination on synthesis.

Similarly, synthesis reactions using fluorescent analogs that were illuminated at a nonexciting wavelength showed little or no impact on polymerase activity, again, indicating that the excited and/or fluorescing analog mediated the damage to the polymerase activity in some measure. The various above-described experiments indicated that photodamage was greatest in the reactions that included the Alexa568 dye labeled nucleotide analogs, further bolstering the suggested photophysical effect, as the Alexa568 dye is reported to be less photostable than the Alexa 488 dye. Additional experiments using non-incorporatable dye labeled analogs, e.g., not complementary to any base in the template, provided little or no measurable photodamage. All of the foregoing provides further apparent indication that the impact on polymerase activity results from the presence of an excited dye labeled nucleotide (or nucleotide analog) within the active site of the polymerase enzyme, indicating some damage to the enzyme or irreversible interaction at the active site.

The experiments using dye labeled tetraphosphates (reaction condition 3, above) were repeated using three different mitigation treatments: (1) 10 mM βME (standard conditions or negative control); (2) 5 mM DTT; and (3) 100 mM MEA, with and without laser illumination as described above. Again, the synthesis products were separated on an agarose gel, an image of which is shown in FIG. 2B. The gel was subjected to image scanning (Molecular Dynamics Typhoon 9400, with Typhoon scanner Control Version 2; gel image quantified with Molecular Dynamiics ImageQuant ver. 5.2). The results of this analysis showed that in the absence of any change from standard conditions, e.g., including only 10 mM βME, the ratio of product when exposed to laser illumination to that in the absence of such illumination was 0.24. When DTT was added to the reaction mixture, the ratio improved to 0.59, while addition of MEA appeared to provide complete or substantially complete protection (a ratio of 1.04) against photo-induced damage from a 5 minute illumination. These data demonstrate that the use of reducing agents as photodamage mitigating agents appear to prevent loss of polymerase activity that occurs during synthesis that is occurring under laser excitation illumination.

Example 2

Photodamage and Mitigation in Surface Immobilized Enzyme Systems

Next, a GST-tagged φ29 polymerase was coated on the surface of a fused silica microscope slide, by depositing the polymerase over the slide and incubating the surface for 15 minutes on ice. Template dependent synthesis of DNA was carried out on the surface using native nucleotides and 10 μM Alexa488-labeled-dC4P and Alexa568-labeled-dT4P, while illuminating a small semi-circular shaped laser spot on the slide. The only reducing agent present in the mixture was 10 mM βME. The slides were exposed to laser illumination at 488 nm (1.1 mW) and 568 nm (1.8 mW) with different positions being illuminated for 1 minute and for 5 minutes. Following illumination, synthesis was allowed to continue for 60 minutes using only native nucleotides. The slides were stained for the presence of synthesized DNA using Sybr-gold. Images of the illuminated slides after 1 minute and 5 minutes are shown in FIG. 3A. As can be seen, the semicircular illumination region is devoid of any synthesized DNA after only 1 minute of illumination, and the impact is shown to be greater after 5 minutes of illumination.

As synthesis was lacking even when non-illuminated synthesis was allowed to proceed for 60 minutes, it is indicative not only of photodamage to polymerase activity, but also that such damage is apparently lasting or even permanent.

Figure 3B:
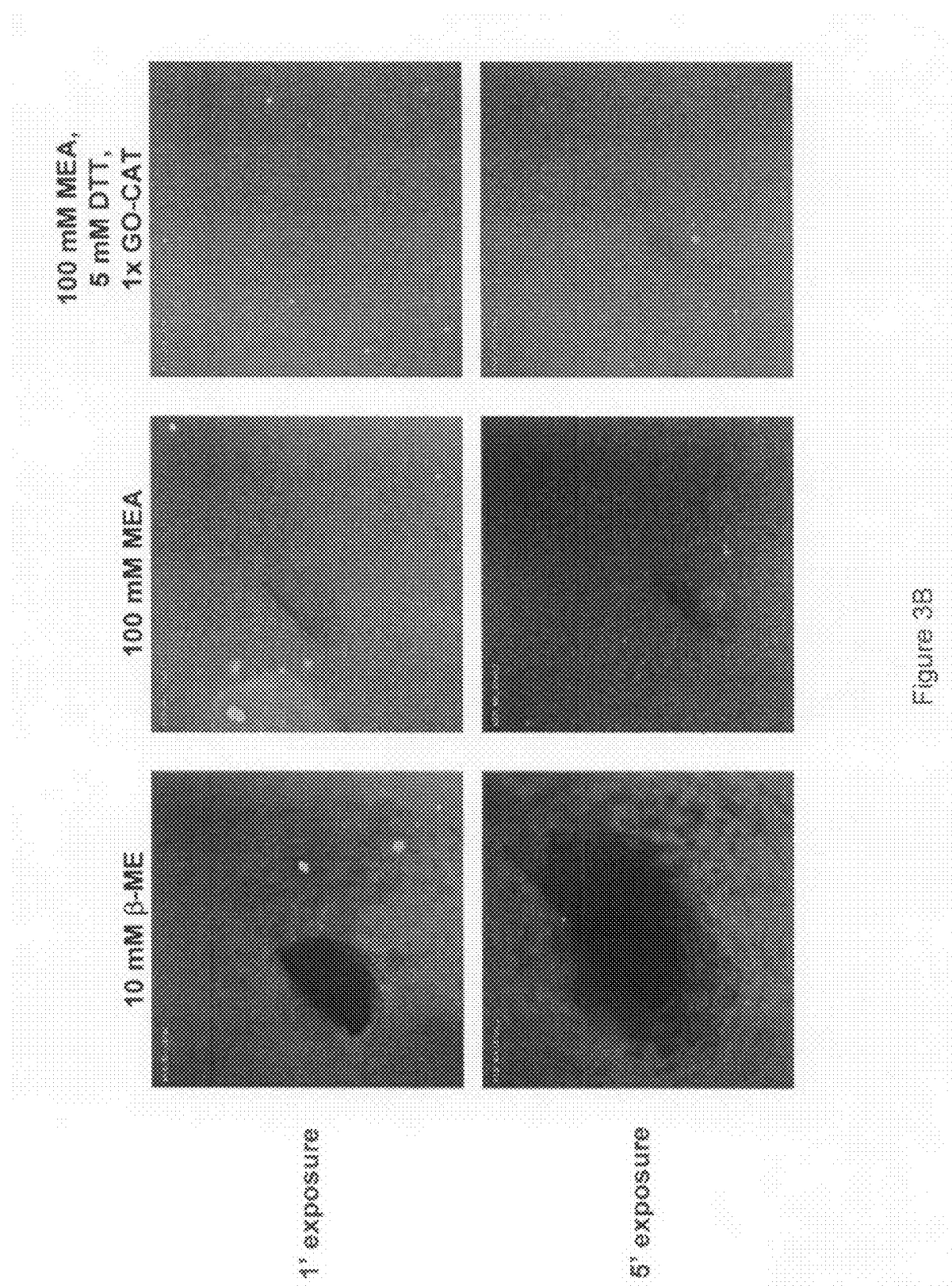

A similar experiment was carried out in the presence of different mixtures of photodamage mitigating agents or concentrations thereof. In particular, as with Example 1, above, three different reaction mixtures were used that included different mitigation treatments: (1) 10 mM βME (standard conditions or negative control) (same as shown in FIG. 3A); (2) 100 mM MEA; and (3) 100 mM MEA, 5 mM DTT and 1×GO Cat (1.3 μM Glucose Oxidase and 150 nM catalase). The results are shown in FIG. 3B. As can be seen, the reactions that included MEA showed a dramatic decrease in the burned in image indicative of damaged polymerase activity, in both 1 minute and 5 minute illumination experiments. The addition of DTT and GO-Cat further reduced the level of damage to polymerase activity to the point that it was not discernible in the 1 minute exposure, and was barely discernible after 5 minutes exposure.

While the presence of GO-Cat provides a substantial elimination of photodamage, the presence of relatively high concentrations of these proteins may have adverse effects on certain applications, e.g., where such reactions are based on relatively low levels of reactants, as such protein can mask, block or otherwise inhibit reactions of interest. As such, an additional experiment was carried out to determine effective reduced levels for the various photodamage mitigating agents on a pretreated surface. Briefly, a surface treated to provide selective polymerase immobilization was prepared and used for the titration experiments on the concentrations of GO-Cat. The experimental set up is set forth below.

A. Surface Preparation

Neutravidin was diluted at 1 mg/ml to 0.2 mg/ml in a solution of 1×BFA (0.05% Tween20, 150 mM KCl, 25 mM Tris-HCl pH 7.5, 5 mM DTT). Biotin-GST tagged (φ29 polymerase was diluted to a concentration of approximately 128 nM in 1×BFA, and equal volumes of the neutravidin solution and polymerase solution were combined and incubated at 23° C. for 30 minutes.

The neutravidin-polymerase mixture was then placed onto a gasketed fused silica slide having a PEG24-Biotin modified surface, and covered with a cover slip. The slide was then incubated for 1 hour at 23° C. Following incubation, the slide was washed 3 times in 1×BFA.

B. Synthesis/Illumination Experiments

Figure 3C:
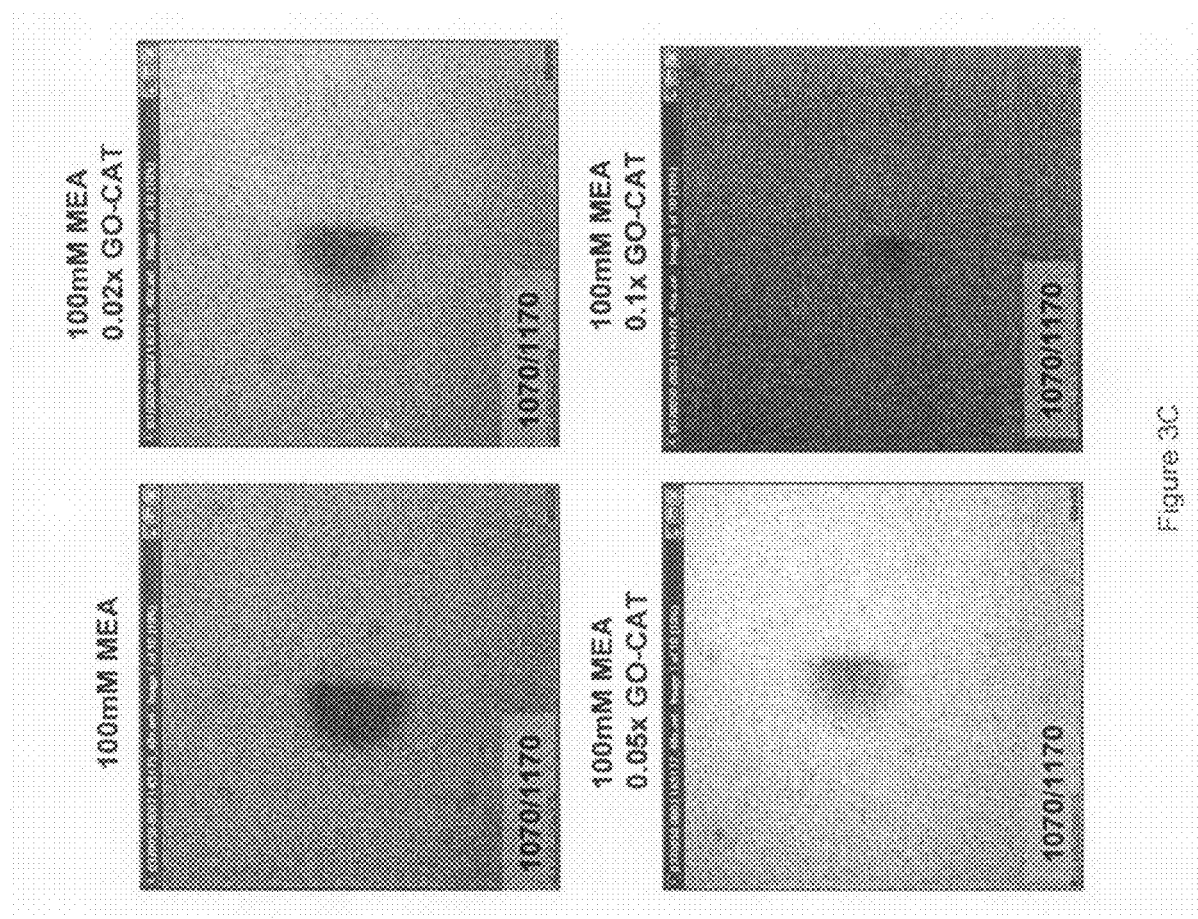
Figure 3D:
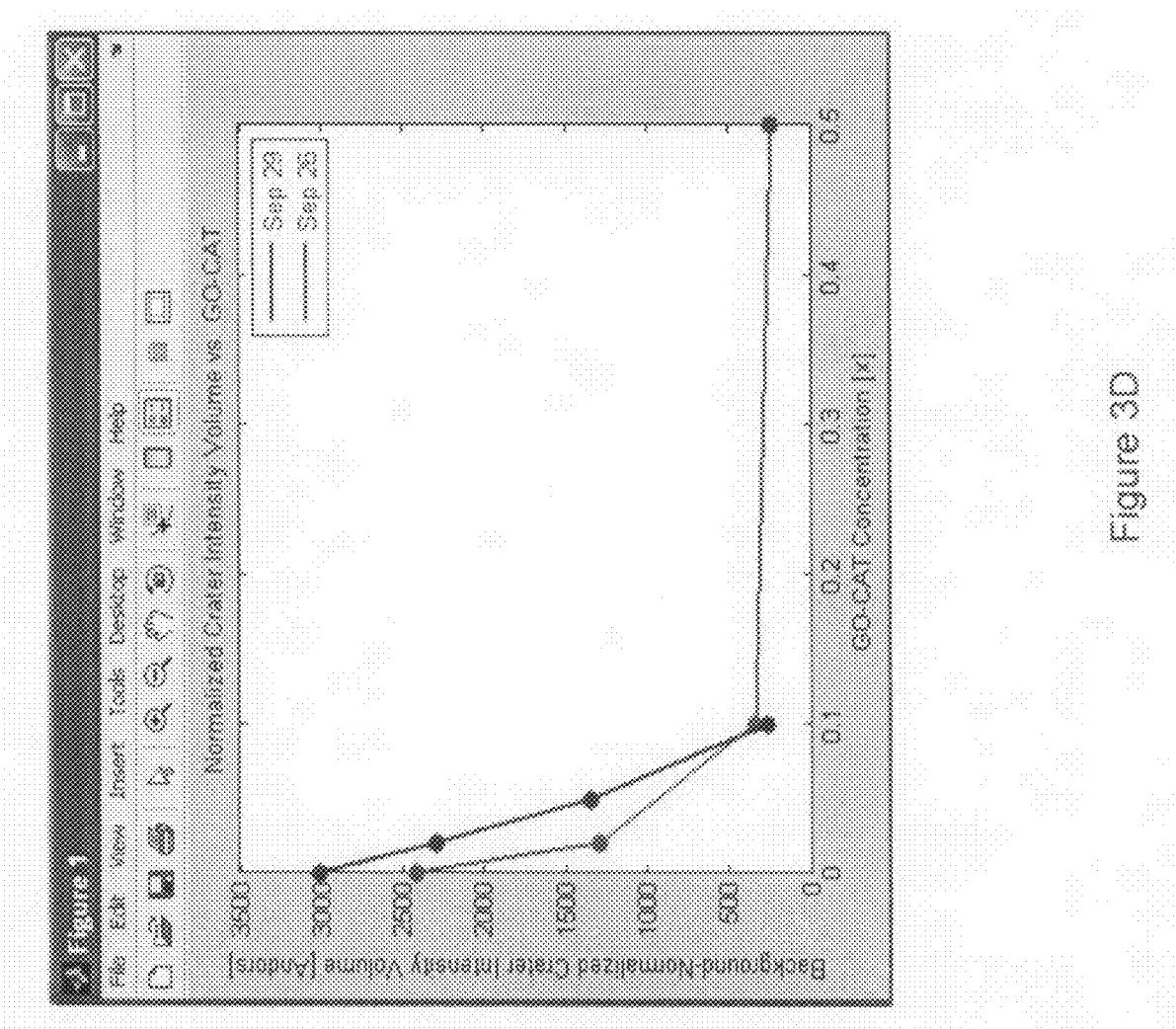
FIG. 3D provides image data plotted as a function of background normalized crater intensity volume vs. GO-Cat concentration.

The GO-Cat reagents were used to dilute with 2×MM reagent (2× prb-BME (100 mM Tris-HCl pH 7.5, 40 mM ammonium sulfate, 150 mM KCl), 200 mM MEA, 10 mM DTT, 0.4% glucose, 1.4 mM $MnCl_2$, 300 nM CL31 circular template, 20 μM A488 dC4P, 20 μM A568 dT4P, 20 μM dATP and dGTP), 1:1 to yield final reaction mixtures having 100 mM MEA, 5 mM DTT, and 0, 0.02×, 0.05× and 0.1×GO-CAT reagent. These diluted synthesis reagents (diluted 2×MM with and without GO-CAT) were then deposited onto the gasketed slide, which was then illuminated at a suitable location with laser spots at 488 nm and 568 nm, for 5 minutes. Following laser illumination, the reaction mixture was replaced with the 1× postMM reagent (1× prb-BME (50 mM Tris-HCl pH 7.5, 20 mM ammonium sulfate, 75 mM KCl), 100 nM CL31 circular template, 0.7 mM MnCl2, 2 μM A488-dUTP, 8 μM dTTP, 10 μM dATP, dCTP and dGTP) and incubated at 23° C. for 60 minutes without illumination. The resulting slide was washed twice with 1×BFA and stained with Sybr® Gold intercalating dye, and imaged. The resulting images are shown in FIG. 3C. As can be seen, use of exceedingly low levels of GO-Cat provides beneficial impact on polymerase activity. However, the presence of the GO-Cat reagents at approximately 0.1× the standard concentration provides nearly complete elimination of polymerase activity damage. The image data was then plotted (FIG. 3D) as a function of background normalized crater intensity volume vs. GO-Cat concentration. Again, suitable protection appears to be achieved at the relatively low added protein level of 0.1×GO-Cat.

Example 3

Photodamage and Mitigation on Nanostructured Reactive Surfaces

Figure 4A:
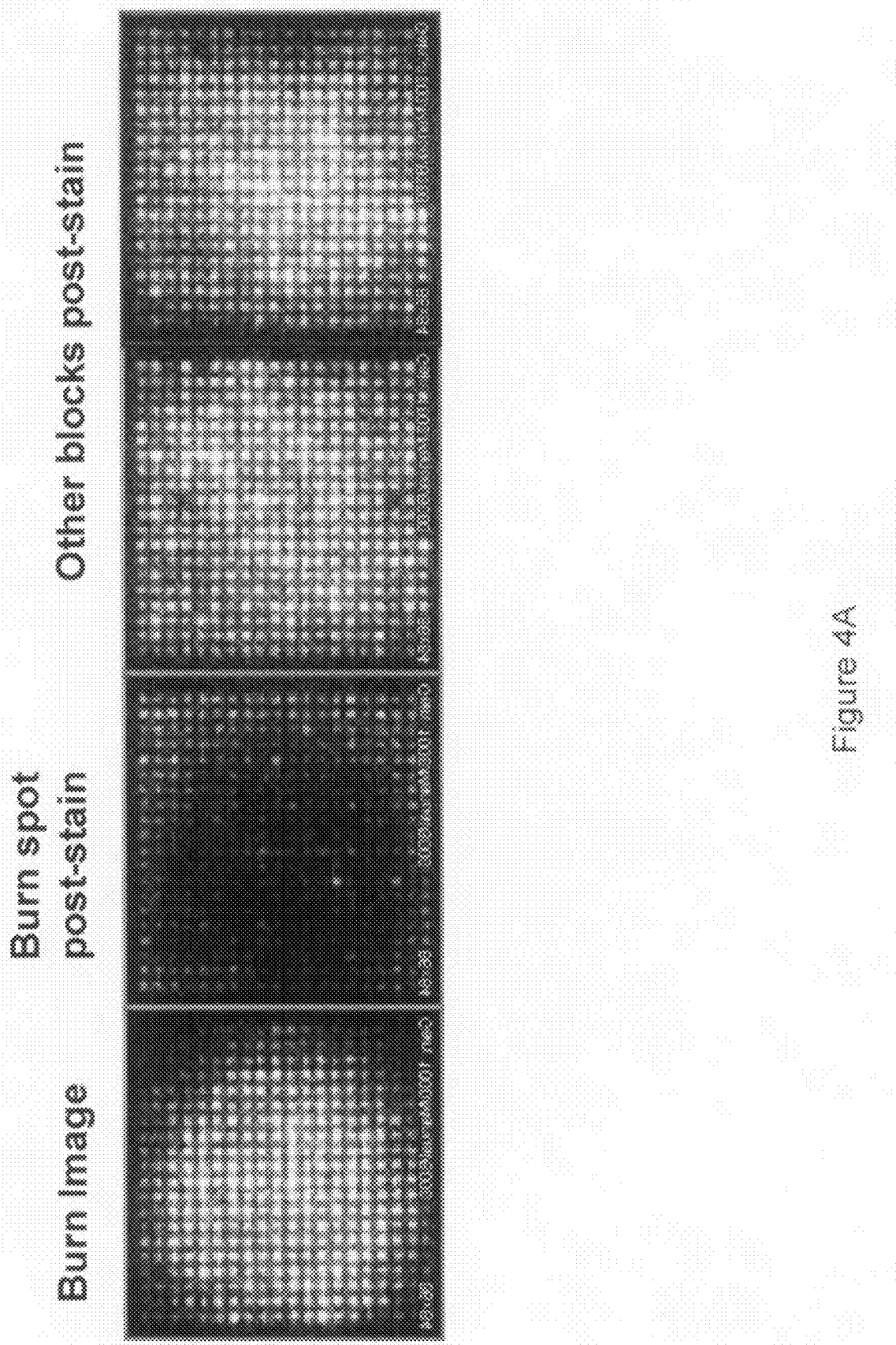
FIG. 4A-4B are images of arrays of zero mode waveguides having immobilized DNA polymerase disposed in the waveguides, and applied in template directed synthesis of DNA using fluorescent nucleotide analogs, while being selectively illuminated with lasers at the fluorescent analogs' excitation wavelengths.

A similar set of experiments to those described above were performed using DNA polymerase immobilized within zero mode waveguides in an array of waveguides. As above, the first experiment was designed to identify whether laser illumination caused damage to immobilized polymerase enzymes on nanostructured surfaces. The surfaces included ZMW arrays in which the polymerase enzyme was adsorbed to the surface. DNA synthesis using dye labeled nucleoside tetraphosphates (Alexa488dC4P and Alexa568dT4P) was carried out with and without laser illumination (at 488 and 568 nm) and the resulting product was again stained with Sybr® Gold. Images of the arrays are shown in FIG. 4A. The illumination profile is shown in the first panel (far left), while the image of the stained DNA product in the illuminated synthesis is shown in the adjacent panel (middle left). As can be seen, a negative image is apparent in the illuminated region corresponding to the illumination pattern. The middle right and far right panels show non-illuminated waveguide arrays, and indicate substantially more DNA is present than in the illuminated sample, again showing photo-induced damage to the polymerase activity in the waveguide arrays.

Figure 4B:
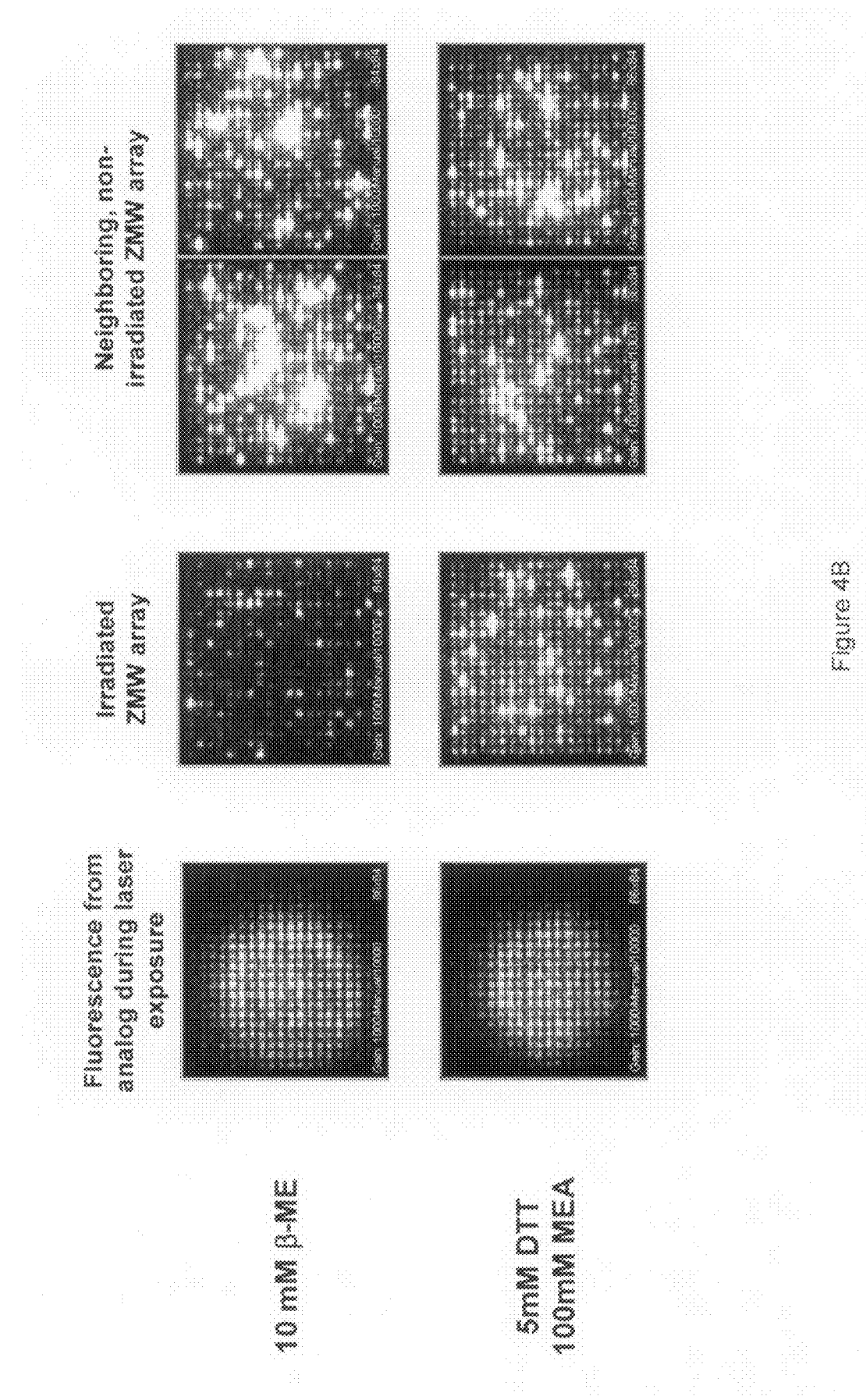

FIG. 4B illustrates a first set of waveguide arrays in which similar synthesis reactions were carried out in the presence of no additional mitigation agents (e.g., only 10 mM βME), or in the presence of 5 mM DTT and 100 mM MEA. As can be seen addition of the DTT and MEA provides substantial protection against damage to polymerase activity caused by laser illumination, and appears to give reactions that produce substantially equivalent amounts of DNA product as the non-illuminated arrays. Additional experiments also showed improvements in the amount of damaged polymerase activity in the presence of 160 mM DTT, without MEA, although not as pronounced as in the presence of 5 mM DTT and 100 mM MEA.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A system for analyzing an illuminated reaction that is susceptible to photodamage, comprising:

a substrate surface having reagents for the reaction disposed thereon, the reagents comprising a first reactant that comprises a polymerase, a second reactant that comprises a fluorescent or fluorogenic substrate for the polymerase, and more than one different photodamage mitigating agent present in a concentration sufficient to reduce photodamage to the polymerase when the first and second reactant are subjected to an excitation illumination for the second reactant, wherein interaction of the first reactant with the second reactant under the excitation illumination causes photodamage to the polymerase in the absence of the more than one different photodamage mitigating agent, a mounting stage supporting the substrate surface and configured to receive the substrate surface;

an optical train positioned to be in optical communication with at least a first portion of the substrate surface to illuminate the first portion of the substrate surface and detect a first set of signals emanating therefrom;

a translation system operably coupled to the mounting stage or the optical train for moving one of the optical train and the substrate surface relative to the other to newly illuminate a second portion of the substrate surface and detect a second set of signals emanating therefrom.

2. The system of claim 1, wherein the fluorescent or fluorogenic substrate comprises at least a first fluorescently labeled nucleotide or nucleotide analog.

3. The system of claim 1, wherein the more than one different photodamage mitigating agent are selected from oxygen scavenging reagents and triplet state quenchers.

4. The system of claim 1, wherein the more than one different photodamage mitigating agent are selected from superoxide dismutase, glucose oxidase/catalase, glutathione peroxidase, ergothioneine, methionine, cysteine, beta-dimethyl cysteine, mercaptopropionylglycine, sodium 2-sulfanylethanesulfonate, glutathione, N-acetyl cysteine, captopril, lycopene, gamma-carotene, astazanthin, canthazanthin, alpha-carotene, beta-carotene, bixin, zeaxanthin, lutein, bilirubin, biliverdin, tocopherols, polyene dialdehydes, melatonin, α-tocopheryl succinate, pyridoxinel, hydrazine, sodium sulfite, hydroxylamine, ascorbic acid, dithiothreitol, mercaptoethylamine, p-mercaptoethanol, n-propyl gallate, p-phenylenediamene, hydroquinone, sodium azide, and diazobicyclooctane.

5. The system of claim 1, wherein the substrate surface comprises a plurality of discrete reaction regions each having reagents for the reaction disposed therein.

6. The system of claim 5, wherein the plurality of discrete reaction regions comprise confined reaction wells.

7. The system of claim 5, wherein the plurality of discrete reaction regions comprise a plurality of zero mode waveguides disposed on the substrate surface.

8. The system of claim 1, wherein the polymerase is a DNA polymerase.

* * * * *